(12) United States Patent
Snow

(10) Patent No.: US 10,682,125 B2
(45) Date of Patent: Jun. 16, 2020

(54) DAMPENED BIOPSY DEVICE AND METHODS OF USE

(71) Applicant: Merit Medical Systems, Inc., South Jordan, UT (US)

(72) Inventor: Jeremy W. Snow, South Jordan, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 413 days.

(21) Appl. No.: 15/057,214

(22) Filed: Mar. 1, 2016

(65) Prior Publication Data

US 2016/0256137 A1 Sep. 8, 2016

Related U.S. Application Data

(60) Provisional application No. 62/128,166, filed on Mar. 4, 2015.

(51) Int. Cl.
*A61B 5/00* (2006.01)
*A61B 10/02* (2006.01)

(52) U.S. Cl.
CPC ...... *A61B 10/0233* (2013.01); *A61B 10/0266* (2013.01); *A61B 2010/0208* (2013.01)

(58) Field of Classification Search
CPC ............ A61B 10/0233; A61B 10/0266; A61B 2010/0208
USPC ...................... 600/562–567, 568; 604/164.05
See application file for complete search history.

(56) References Cited

U.S. PATENT DOCUMENTS

| | | | |
|---|---|---|---|
| 5,036,860 A | 8/1991 | Leigh et al. | |
| 5,172,702 A | 12/1992 | Leigh | |
| 5,601,572 A | 2/1997 | Middlemann et al. | |
| 5,655,542 A | 8/1997 | Weilandt | |
| 5,788,651 A | 8/1998 | Weilandt | |
| 5,800,389 A | 9/1998 | Burney et al. | |
| 5,842,999 A * | 12/1998 | Pruitt ................. | A61B 10/0275 600/562 |
| D418,223 S | 12/1999 | Phipps et al. | |
| 6,045,567 A | 4/2000 | Taylor et al. | |
| D428,150 S | 7/2000 | Ruf et al. | |
| 6,126,617 A | 10/2000 | Weilandt et al. | |
| 6,196,978 B1 | 3/2001 | Weilandt et al. | |
| 6,273,861 B1 | 8/2001 | Bates et al. | |

(Continued)

FOREIGN PATENT DOCUMENTS

| | | |
|---|---|---|
| AT | 366546 | 6/1976 |
| EP | 0966920 B1 | 4/2004 |

(Continued)

OTHER PUBLICATIONS

International Search Report and Written Opinion dated Jul. 1, 2016 for PCT/US2016/020165.

(Continued)

*Primary Examiner* — May A Abouelela
(74) *Attorney, Agent, or Firm* — Stoel Rives LLP

(57) ABSTRACT

An impact biopsy device is disclosed. The impact biopsy device may be configured to displace various cutting elements, such as an outer tubular member and cutting element and a cannula to sever a tissue sample from a patient. The impact biopsy device may comprise an actuation system configured to transfer displacement or force to the cutting elements by the impact of an element on another element.

20 Claims, 8 Drawing Sheets

(56) References Cited

U.S. PATENT DOCUMENTS

| | | |
|---|---|---|
| 6,322,523 B2 | 11/2001 | Weilandt et al. |
| 6,358,217 B1 | 3/2002 | Bourassa |
| D457,955 S | 5/2002 | Bilitz |
| 6,419,641 B1 | 7/2002 | Mark et al. |
| D463,555 S | 9/2002 | Etter et al. |
| 6,488,662 B2 | 12/2002 | Sirimanne |
| 6,497,687 B1 | 12/2002 | Blanco |
| D490,152 S | 5/2004 | Myall et al. |
| 7,041,065 B2 | 5/2006 | Weilandt et al. |
| 7,247,160 B2 | 7/2007 | Seiler et al. |
| D571,009 S | 6/2008 | Smith et al. |
| 7,470,237 B2 | 12/2008 | Beckman et al. |
| D586,916 S | 2/2009 | Faulkner et al. |
| D598,543 S | 8/2009 | Vogel et al. |
| 7,608,048 B2 | 10/2009 | Goldenberg |
| D612,044 S | 3/2010 | Scheibe |
| D612,051 S | 3/2010 | Ruf |
| 7,740,593 B2* | 6/2010 | Shabaz ............... A61B 17/3403 600/562 |
| D619,251 S | 7/2010 | Justiniano-Garcia et al. |
| D628,293 S | 11/2010 | Ruf |
| 8,137,287 B2* | 3/2012 | Cooke ................ A61B 10/0275 600/562 |
| 8,137,317 B2 | 3/2012 | Osypka |
| 8,480,595 B2* | 7/2013 | Speeg ................ A61B 10/0275 600/568 |
| 9,392,998 B2* | 7/2016 | Snow ................. A61B 10/0266 |
| 2001/0009979 A1 | 7/2001 | Weilandt et al. |
| 2004/0097832 A1* | 5/2004 | Adams ............... A61B 10/0275 600/564 |
| 2004/0133124 A1 | 7/2004 | Bates et al. |
| 2004/0215103 A1 | 10/2004 | Mueller et al. |
| 2004/0267157 A1* | 12/2004 | Miller ................. A61B 10/025 600/565 |
| 2005/0054947 A1* | 3/2005 | Goldenberg ....... A61B 10/0233 600/567 |
| 2005/0125017 A1 | 6/2005 | Kudma et al. |
| 2006/0085019 A1 | 4/2006 | Cote et al. |
| 2006/0089565 A1* | 4/2006 | Schramm ........... A61B 10/0275 600/568 |
| 2006/0155210 A1 | 7/2006 | Beckman et al. |
| 2007/0027407 A1 | 2/2007 | Miller |
| 2007/0078472 A1 | 4/2007 | Singh |
| 2007/0142743 A1* | 6/2007 | Provencher ........ A61B 10/0266 600/562 |
| 2007/0142744 A1 | 6/2007 | Provencher |
| 2007/0179403 A1 | 8/2007 | Heske et al. |
| 2007/0250037 A1 | 10/2007 | Brimhall et al. |
| 2008/0200833 A1 | 8/2008 | Hardin et al. |
| 2008/0200835 A1 | 8/2008 | Monson et al. |
| 2008/0228104 A1 | 9/2008 | Uber et al. |
| 2008/0281223 A1 | 11/2008 | Goldenberg |
| 2008/0281226 A1* | 11/2008 | Peters ................... A61B 10/02 600/567 |
| 2008/0300507 A1 | 12/2008 | Figueredo et al. |
| 2009/0043262 A1* | 2/2009 | Snow .................. A61M 5/3271 604/198 |
| 2009/0143698 A1 | 6/2009 | Janssens |
| 2009/0259200 A1 | 10/2009 | Lampropoulos et al. |
| 2009/0299220 A1* | 12/2009 | Field .................. A61B 10/0275 600/567 |
| 2010/0130887 A1 | 5/2010 | Selis |
| 2010/0168773 A1 | 7/2010 | Funderburk et al. |
| 2011/0004121 A1* | 1/2011 | Drubetsky ......... A61B 10/0233 600/567 |
| 2011/0152715 A1 | 6/2011 | Delap et al. |
| 2011/0201964 A1* | 8/2011 | Speeg ................ A61B 10/0275 600/562 |
| 2011/0251631 A1 | 10/2011 | Trees et al. |
| 2012/0220894 A1 | 8/2012 | Melsheimer |
| 2013/0131548 A1 | 5/2013 | McGhie et al. |
| 2013/0150795 A1 | 6/2013 | Snow et al. |
| 2013/0324910 A1 | 12/2013 | Ohri et al. |
| 2014/0100479 A1 | 4/2014 | Tripp et al. |
| 2014/0171826 A1 | 6/2014 | Lampropoulos et al. |
| 2014/0207021 A1 | 7/2014 | Snow |
| 2015/0201963 A1 | 1/2015 | Snow |
| 2015/0045828 A1 | 2/2015 | McArthur et al. |
| 2015/0094751 A1 | 4/2015 | Chen et al. |
| 2015/0201917 A1 | 6/2015 | Snow |

FOREIGN PATENT DOCUMENTS

| | | |
|---|---|---|
| EP | 1679039 | 7/2006 |
| WO | 199622733 | 8/1996 |
| WO | 199944505 | 9/1999 |
| WO | 2006013389 | 2/2006 |
| WO | 2012167216 A2 | 12/2012 |
| WO | 2014100349 | 6/2014 |
| WO | 2014113665 | 7/2014 |

OTHER PUBLICATIONS

Extended European Search Report dated Jul. 26, 2016 for EP14741114.4.
Office Action dated Mar. 26, 2018 for U.S. Appl. No. 15/184,551.
International Search Report and Written Opinion dated Apr. 3, 2014 for PCT/US2013/076418.
International Search Report and Written Opinion dated Apr. 27, 2015 for PCT/US2015/011746.
International Search Report and Written Opinion dated Apr. 30, 2015 for PCT/US2015/012002.
International Search Report and Written Opinion dated May 1, 2014 for PCT/US2014/012043.
International Search Report and Written Opinion dated Jun. 23, 2015 for PCT/US2013/076418.
Office Action dated Jun. 1, 2016 for U.S. Appl. No. 14/134,280.
Shuttle® and CT-Core® Semi-Automatic Devices Updated to the website between Nov. 8, 2012-Jan. 24, 2013. Accessed website on Jun. 27, 2014 at http://www.healthcare.com/qb/int_radiplogy.html.
European Search Report dated Aug. 30, 2018 for EP16759335.9.
Office Action dated Feb. 26, 2019 for U.S. Appl. No. 15/184,551.
Office Action dated Oct. 9, 2018 for U.S. Appl. No. 15/184,551.
Notice of Allowance dated Oct. 23, 2019 for U.S. Appl. No. 15/184,551.

* cited by examiner

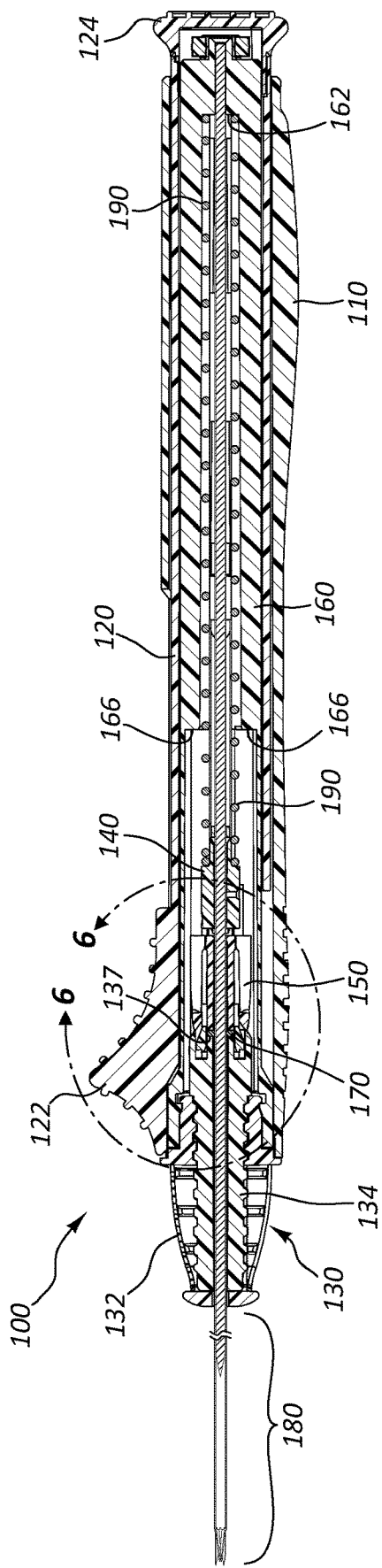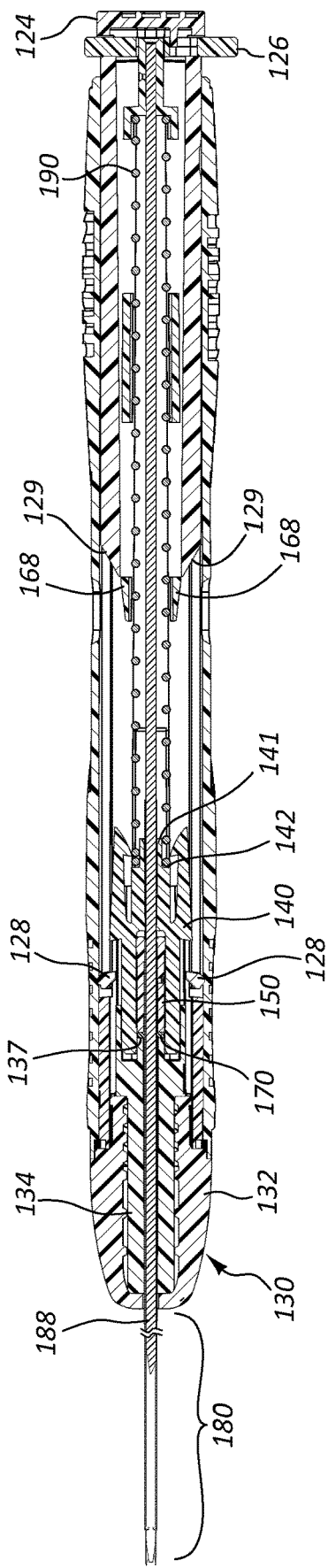

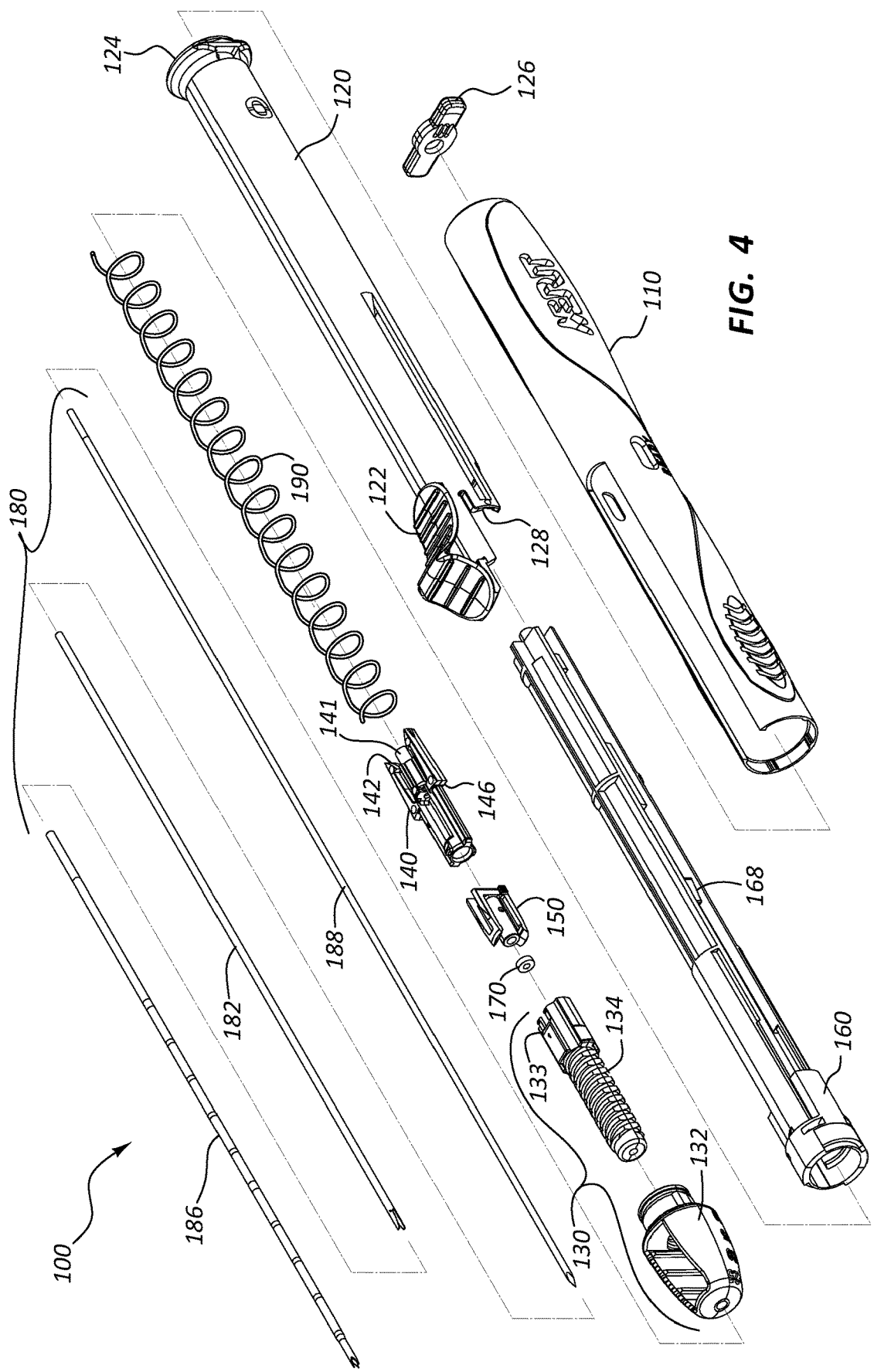

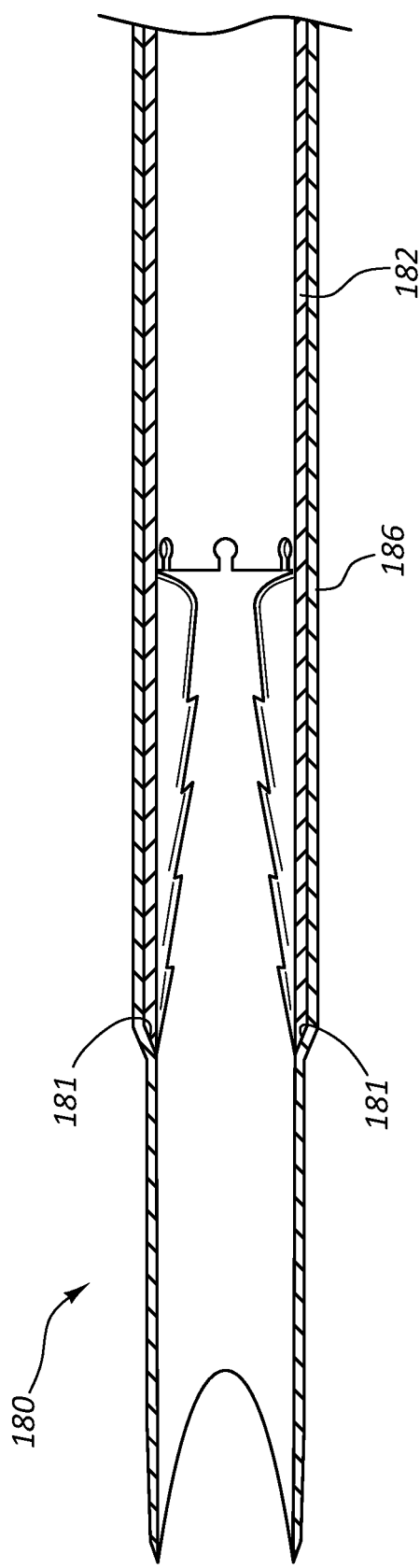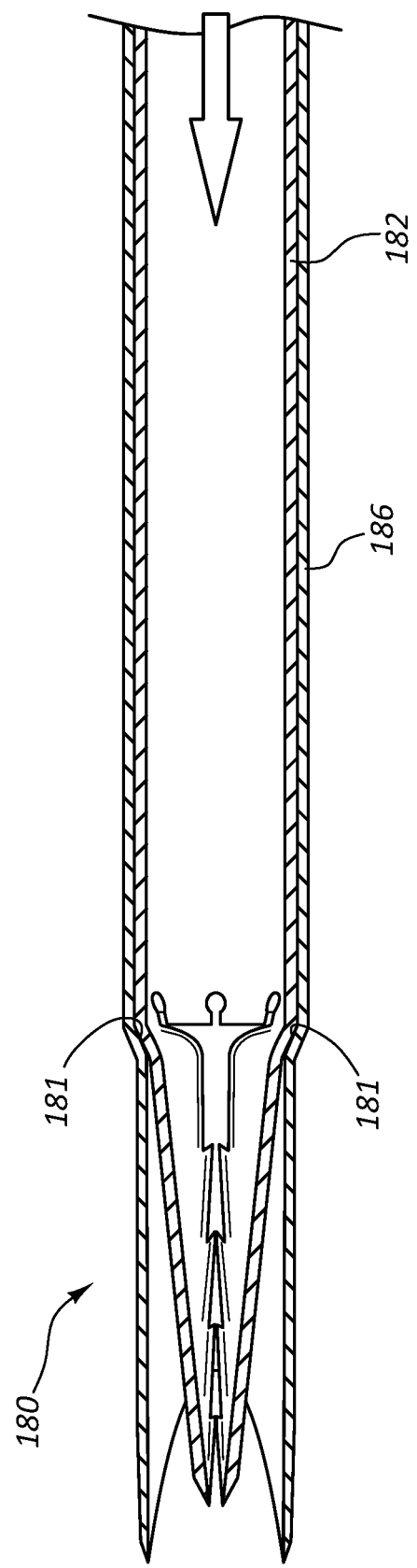

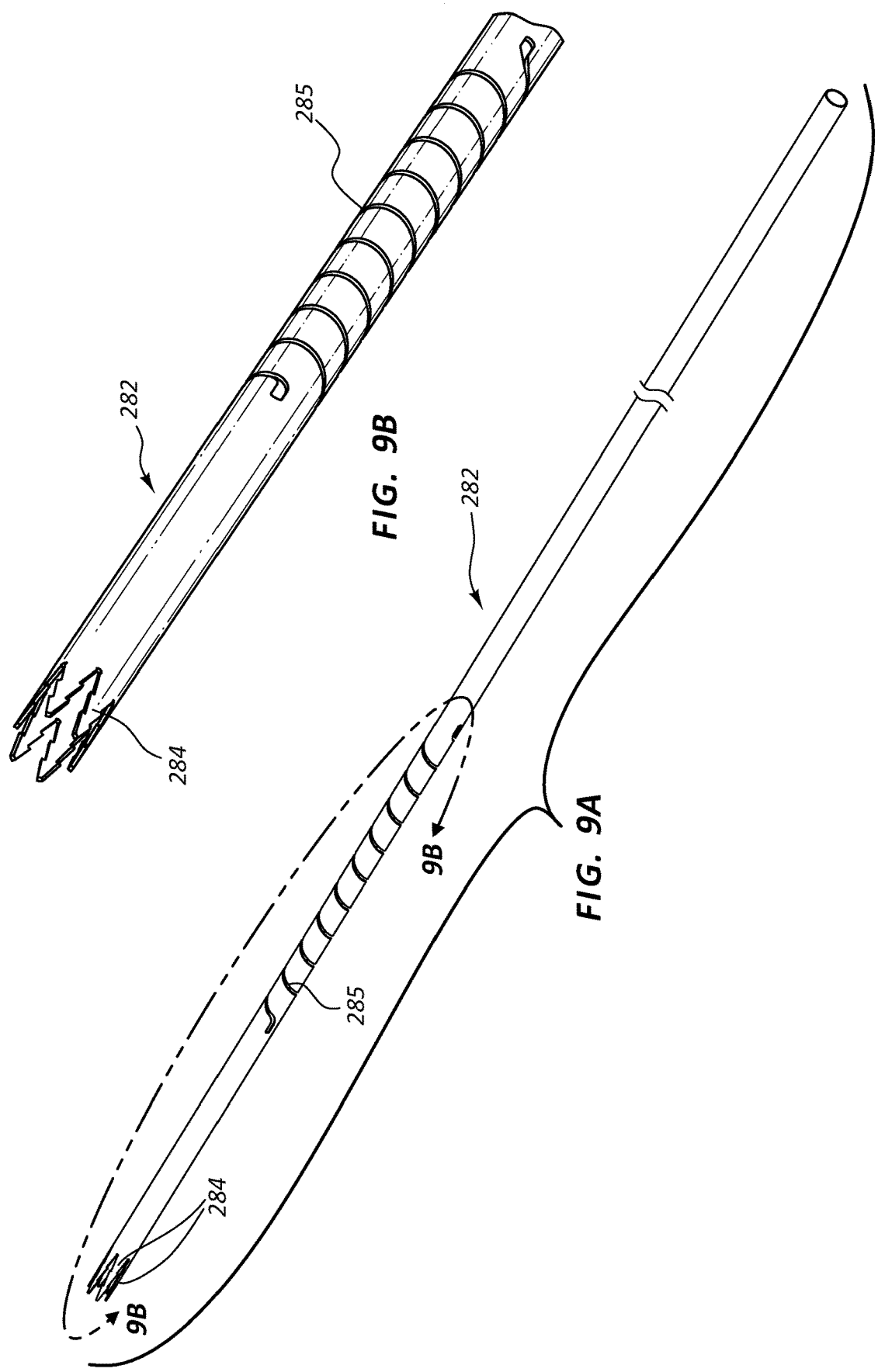

DAMPENED BIOPSY DEVICE AND METHODS OF USE

RELATED APPLICATIONS

This application claims priority to U.S. Provisional Patent Application No. 62/128,166, filed on Mar. 4, 2015 and titled "Dampened Biospy Device and Method of Use," which is hereby incorporated by reference in its entirety.

TECHNICAL FIELD

The present disclosure relates generally to medical devices. More specifically, the present disclosure relates to biopsy devices, including biopsy devices configured with an impact driven or kinetic energy operation system, including systems comprising dampening components.

BRIEF DESCRIPTION OF THE DRAWINGS

The embodiments disclosed herein will become more fully apparent from the following description and appended claims, taken in conjunction with the accompanying drawings. The drawings depict only typical embodiments, which embodiments will be described with additional specificity and detail in connection with the drawings in which:

FIG. 2 is a first cross-sectional view of the biopsy device of FIG. 1, taken through plane 2-2.

FIG. 3 is a second cross-sectional view of the biopsy device of FIG. 1, taken through plane 3-3.

FIG. 4 is an exploded view of the biopsy device of FIG. 1.

FIG. 8A is a cross-sectional view of a portion of the needle assembly of FIG. 7, in a primed configuration.

FIG. 8B is a cross-sectional view of a portion of the needle assembly of FIG. 7, in a triggered configuration.

FIG. 9A is a perspective view of another embodiment of a pincer component of a needle assembly, analogous to the needle assembly of FIG. 1.

FIG. 9B is a detail view of a distal end portion of the pincer of FIG. 9A, taken through line 9B-9B.

DETAILED DESCRIPTION

Figure 1:
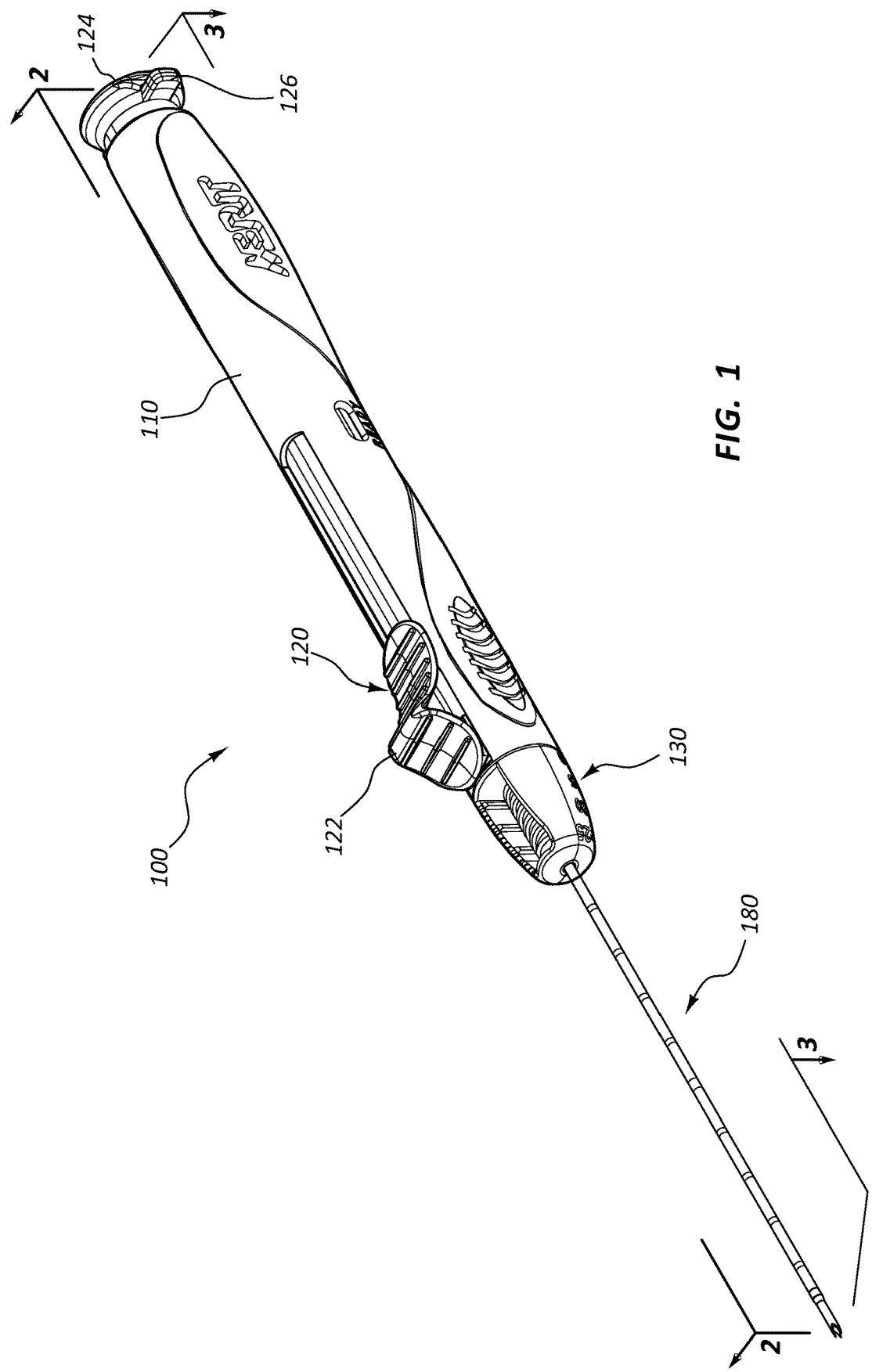
FIG. 1 is a perspective view of a biopsy device in a fired configuration.

Biopsy devices may be configured to retrieve tissue samples from various locations within a patient's body. For example, a biopsy device may comprise a needle assembly including cannulas or other cutting members configured to sever a tissue sample. The needle assembly may be advanced to a location within the body through the skin of the patient (percutaneous access) or may be advanced through a body lumen or other structure.

Furthermore, a biopsy device may comprise an actuation mechanism configured to displace the needle assembly such that the needle assembly severs the targeted tissue sample. Biasing mechanisms such as springs, triggers, and so forth may be configured to allow a practitioner to manipulate various components of a needle assembly through manipulating the actuation mechanism. In addition to mechanical biasing mechanisms such as springs, compressed gas or other energy sources may be configured to power a biopsy device. In some embodiments, for example, a compressed $CO_2$ cartridge may be used to power a biopsy device.

Regardless of the energy source, a mechanism may be configured such that, once the needle assembly is disposed adjacent tissue to be biopsied, actuation of a single trigger may cause various components of a needle assembly to be displaced to sever a tissue sample. Biasing elements or other energy sources within the actuation mechanism may provide the force required to advance the needle assembly components, and other mechanisms may control the relative displacement of individual components of a needle assembly.

As further disclosed below, a biopsy device may comprise components configured to actuate the biopsy device through transfer of kinetic energy between components, including instances where one or more components are displaced due to an impact force.

Additionally, a biopsy device may comprise one or more dampening components configured to absorb or dampen energy associated with acceleration/deceleration of components of the device, impact between components, oscillation, sound, and so forth. Dampening members may comprise discrete elements or may be a feature of any other component.

It will be readily understood that the components of the embodiments as generally described and illustrated in the figures herein could be arranged and designed in a wide variety of configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

The phrases "connected to" and "coupled to" refer to any form of interaction between two or more entities, including mechanical, electrical, magnetic, electromagnetic, fluidic, and thermal interaction. Two components may be coupled to each other even though they are not in direct contact with each other. For example, two components may be coupled to each other through an intermediate component.

The directional terms "proximal" and "distal" are used herein to refer to opposite locations on a medical device. The proximal end of the device is defined as the end of the device closest to the practitioner when the device is in use by the practitioner. The distal end is the end opposite the proximal end, along the longitudinal direction of the device, or the end furthest from the practitioner.

FIG. 1 is a perspective view of an impact biopsy device 100 in a fired configuration. In other words, and as further detailed below, in the configuration of FIG. 1, elements of the biopsy device 100 are disposed in relative positions corresponding with the state of the biopsy device 100 after it has been actuated to obtain a tissue sample. The biopsy device 100 may comprise a body member 110 that may be configured to be grasped by a practitioner when the biopsy device 100 is in use. Thus, in some embodiments the body member 110 may comprise a handle or grip. The biopsy device 100 may also comprise an actuator 120. The actuator 120 may be configured to prime and/or trigger the biopsy device 100. Embodiments wherein the actuator 120 comprises an assembly of subelements are also within the scope of this disclosure. For instance, one element of a subassembly may comprise a priming component while a separate element may comprise a trigger component. In the illustrated embodiment, the actuator 120 comprises a distal input 122 and a proximal input 124. In the illustrated embodiment, these inputs 122, 124 are portions of a single actuator 120 comprising an integral single member; in other embodiments one or both may comprise a subelement.

Additionally, and as further discussed below, displacement of the actuator 120 with respect to the body member 110 may be configured to prime the biopsy device 100. Further displacement of the actuator 120 with respect to the body member 110 when the biopsy device 100 is in a primed configuration may trigger or release the biopsy device 100. Triggering the device may actuate elements within the body member 110, such as components of an needle assembly 180, in connection with obtaining a tissue sample.

The illustrated embodiment further comprises a safety tab 126 operably coupled to the actuator 120. Manipulation of the safety tab 126 may prevent inadvertent triggering of the biopsy device 100 by locking the actuator 120 to prevent triggering when the safety tab 126 is in a locked position.

Additionally, the biopsy device 100 may comprise an adjustable stop assembly 130. Displacement of one or more components of the adjustable stop assembly 130 may adjust or control the length of the tissue sample severed by the biopsy device 100.

FIG. 2 is a first cross-sectional view of the biopsy device 100 of FIG. 1, and FIG. 3 is a second cross-sectional view of the impact biopsy device 100 of FIG. 1. FIG. 4 is an exploded view of the biopsy device 100 of FIG. 1. As shown in FIGS. 2-4, the biopsy device 100 may include an actuation assembly comprised of components configured to displace a needle assembly or other cutting members. As used herein, the actuation assembly refers generally to components configured to transfer energy to cutting members coupled to the biopsy device 100. Exemplary cutting members include needles, trocars, cannulas, and so forth.

In the embodiment of FIGS. 1-4, a needle assembly 180 is coupled to the biopsy device 100. It is within the scope of this disclosure to couple any variety of needles, cannulas, trocars, stylets, or other instruments to the biopsy device 100. For example, a stylet and cannula configured to sever a partial core tissue sample may be operably coupled to the biopsy device 100. Further, one or more cannulas configured to obtain a full core tissue sample may be operably coupled to the biopsy device 100. In some embodiments, one or more elements of a needle or cutting assembly may be coupled to components within the body member 110 of the biopsy device 100 and may extend from the body member 110 through a lumen in the adjustable stop assembly 130.

In the embodiment of FIGS. 1-3, the biopsy device 100 is disposed in an fired configuration, corresponding to the state of the device after it has been actuated to obtain a sample. Thus, in the configuration of FIGS. 1-3, the biopsy device 100 cannot be triggered to obtain a sample without first priming the biopsy device 100. For example, the biopsy device 100 may comprise a biasing element, such as a spring 190. In the fired configuration, the spring 190 may be uncompressed. After priming, and in the primed configuration, the spring 190 may be compressed or loaded such that potential energy is stored within the spring 190. When in the primed configuration, the biopsy device 100 is ready to be actuated. Additionally, the biopsy device 100 may be configured to be disposed in an initial configuration. An initial configuration, such as an initial shipping configuration, the spring 190 may be unloaded though the needle assembly 180 may not be disposed in a fully actuated position, while in the fired configuration the spring 190 may be unloaded and the needle assembly 180 fully actuated, with the needle assembly 180 components in relative positions corresponding to a state following severing of a tissue sample. Positions of the members of the needle assembly 180 in the fired, primed, and initial configurations are further detailed below.

Referring to FIGS. 2 and 3, the biopsy device 100 may comprise a first hub member, such as pincer hub 140. The pincer hub 140 may be coupled to a pincer member 182 of the needle assembly 180. Accordingly, displacement of the pincer hub 140 may also displace the pincer member 182. In the illustrated embodiment, the spring 190 is disposed between the pincer hub 140 and a housing spring surface 162 of a housing member 160. In the depicted embodiment the housing member 160 is coupled to the body member 110.

Again, in the illustrated fired configuration, the spring 190 is at least partially unloaded. As used herein, priming the biopsy device 100 refers to displacement of various elements of the biopsy device 100 to transition the biopsy device 100 from the initial configuration into a primed configuration, meaning a configuration where the spring 190 is compressed and the biopsy device 100 may be triggered to obtain a sample.

Figure 5A:
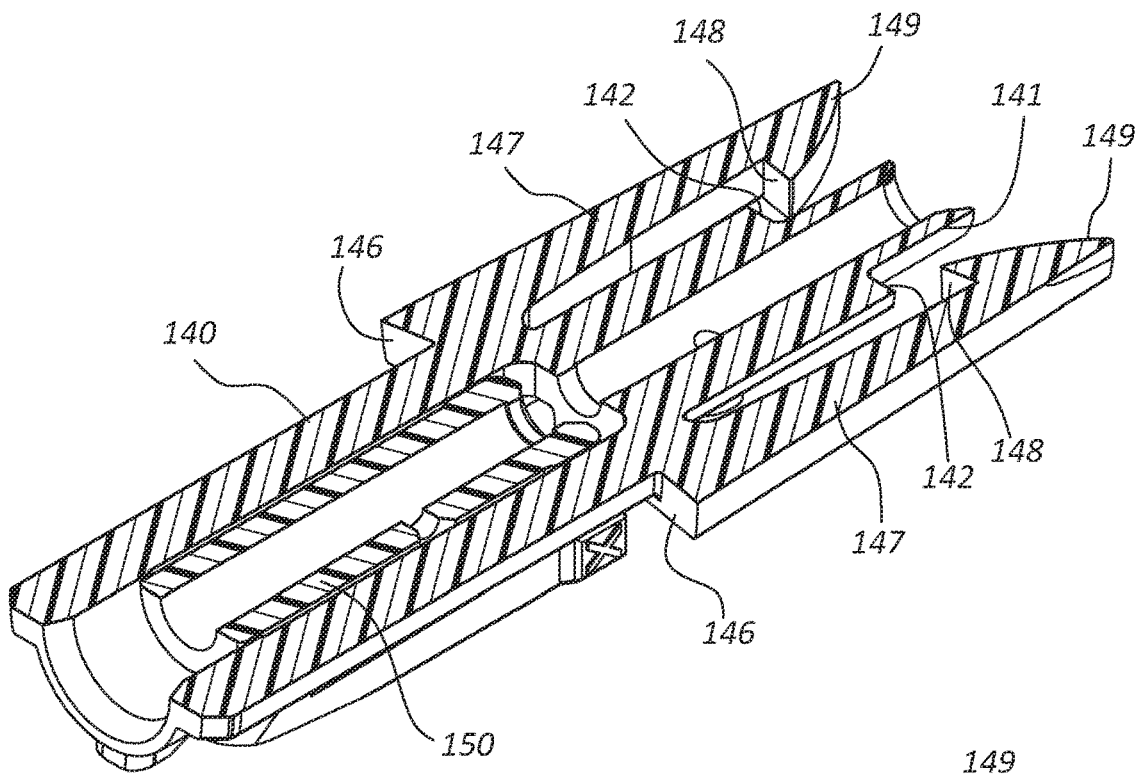
FIG. 5A is a first enlarged cross-sectional view of a portion of the biopsy device of FIG. 1, taken through a first plane.
Figure 5B:
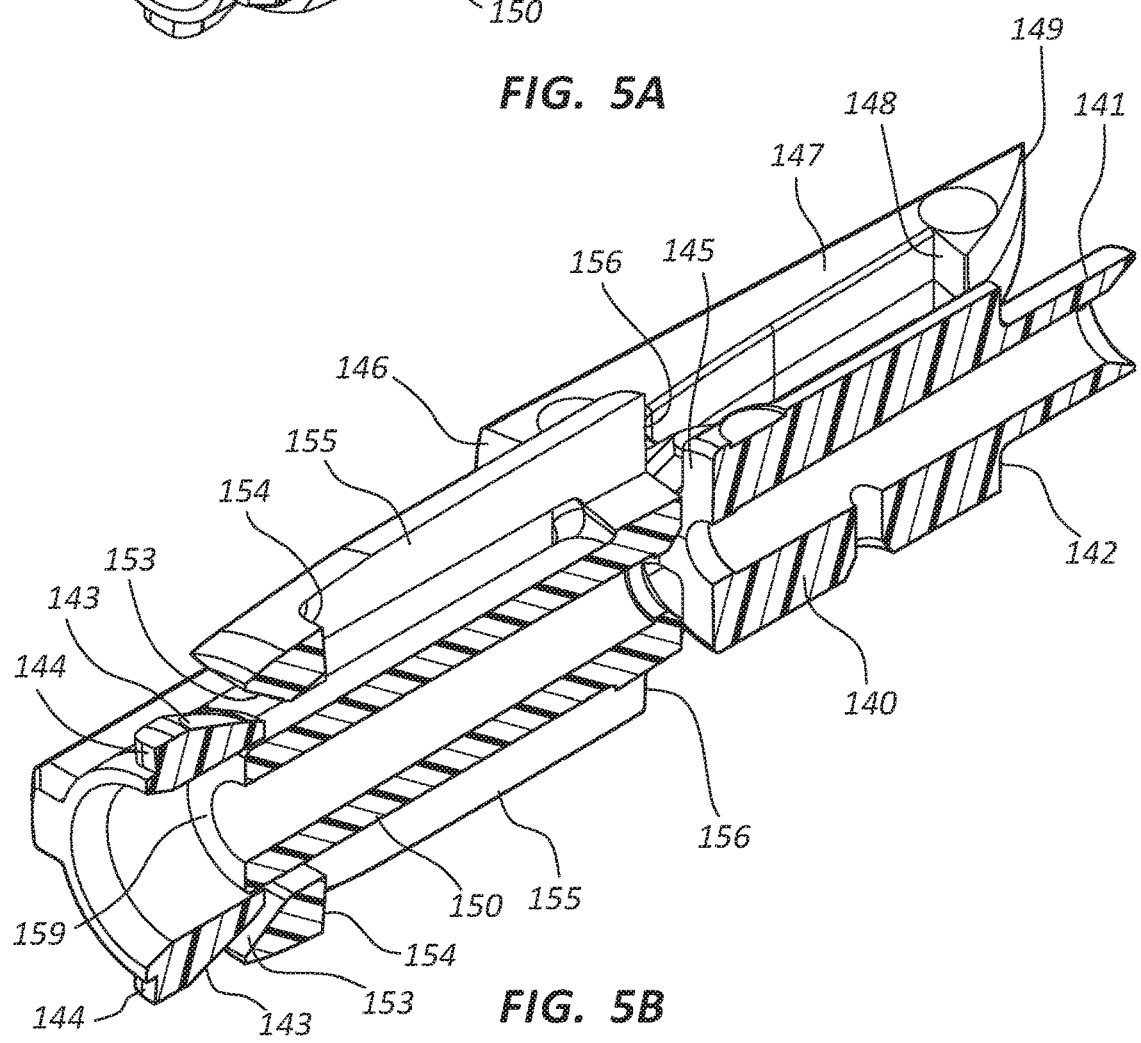
FIG. 5B is a second enlarged cross-sectional view of the portion of the biospy device of FIG. 5A, taken through a second plane orthogonal to the first plane.

FIG. 5A is a first enlarged cross-sectional view of a the pincer hub 140 and needle hub 150 of the dampened biopsy device 100, in the same relative positions as shown in FIGS. 2-4, taken through a first plane. FIG. 5B is a second enlarged cross-sectional view of the pincer hub 140 and needle hub 150 of FIG. 5A, taken through a second plane orthogonal to the first plane.

As shown in FIGS. 2-4 and FIGS. 5A-5B, the pincer hub 140 comprises actuator catches 146 disposed to interact with pincer hub catches 128 on the actuator 120. In operation, a user may draw back the actuator 120 with respect to the body member 110, the actuator moving in a proximal direction. This proximal displacement of the actuator 120 transitions the biopsy device 100 from the fired configuration into a primed configuration. Similarly, manipulation of the biopsy device 100 from an initial configuration into the primed configuration may also be done by priming the biopsy device. As the actuator 120 is displaced proximally, the pincer hub catches 128 of the actuator 120 interact with the actuator catches 146 of the pincer hub 140, also drawing the pincer hub 140 back in a proximal direction. This displacement of the pincer hub 140 compresses the spring 190 between the spring surface 162 of the housing member 160 and the pincer hub 140. The pincer hub 140 may comprise a pincer hub spring surface 142, which may comprise one or more projections from a central protrusion 141 of the pincer hub 140. The spring 190 may be disposed at least partially around the central protrusion 141 and compressed by interaction with the pincer hub spring surface 142 when in a primed configuration. When the biopsy device 100 is in a primed configuration, the spring 190 stores potential energy that may be released when the biopsy device is triggered.

Additionally, as the biopsy device 100 is primed, interaction between the pincer hub 140 and the needle hub 150 may also displace the needle hub 150. For example, priming the biopsy device 100 may also proximally displace the needle hub 150. In the depicted embodiment, the needle hub 150 is coupled to the needle 186 of the needle assembly 180, thus displacement of the needle hub 150 also displaces the needle.

Still referencing FIGS. 2-5B, the pincer hub 140 comprises a pincer hub angled surface 143 which may interact with a needle hub angled surface 153 of the needle hub 150 as the pincer hub 140 is drawn back in a proximal direction. As the pincer hub 140 is drawn back, interaction between the pincer hub angled surface 143 and the needle hub angled surface 153 may draw back the needle hub 150 until needle hub stop surfaces 156 contact housing shoulder 166. Interaction between the needle hub stop surfaces 156 and the housing shoulder 166 may prevent further proximal displacement of the needle hub 150.

Once proximal displacement of the needle hub 150 is arrested by the housing shoulder 166, the pincer hub angled surface 143 and needle hub angled surface 153 may interact to radially displace the needle hub arms 155, allowing the pincer hub angled surface 143 to move proximally beyond the needle hub angled surface 153 until the pincer hub distal shoulder 144 is proximal of the needle hub distal catches 154. At that point, the needle hub arms 155 return from the radially outward position. In some instances there may be sufficient resistance to proximal displacement of the needle hub 150 to allow the pincer hub angled surface 143 to move proximally beyond the needle hub angled surface 153 until the pincer hub distal shoulder 144 is proximal of the needle hub distal catches 154 before the needle hub 150 contacts the housing shoulder 166. In such instances, the needle hub 150 will still be drawn back to into contact with the housing shoulder 166, though the pincer hub distal shoulder distal should 144 and needle hub distal catches 154 engage prior to contact between the needle hub 150 and the housing shoulder 166. For instance, as further detailed below, after firing the needle hub 150 may contact the release member 134. In some instances, interaction between the release member 134 and the needle hub 150 may initially resist proximal displacement of the needle hub, for example.

The pincer hub 140 is further drawn back, creating an offset between the pincer hub distal shoulder 144 and the needle hub distal catches 154 when the biopsy device 100 reaches a primed configuration.

The pincer hub 140 is drawn back proximally until the pincer hub proximal catches 148 engage with priming catches 168 of the housing member 160. To accommodate proximal displacement of the pincer hub proximal catches 148 past the priming catches 168, the pincer hub arms 147 may temporarily displace radially outward. Angled surfaces associated with one or both of the pincer hub arms 147 and the priming catches 168 may facilitate this displacement. Engagement of the pincer hub proximal catches 148 with the priming catches 168 may then prevent distal displacement of the pincer hub 140, allowing a user to release the actuator 120 without releasing tension on the spring 190. The biopsy device 100 is then in a primed configuration.

Transition of the biopsy device 100 to release the spring 190 is referred to as triggering the biopsy device 100. Upon triggering of the biopsy device 100, components of the actuation assembly may, in turn, displace components of the needle assembly 180 to obtain a tissue sample. Again, the actuation assembly refers generally to components configured to transfer energy to cutting members coupled to the biopsy device 100. In the depicted embodiment, the actuation assembly comprises the pincer hub 140, the needle hub 150, and the spring 190, among other components.

To trigger the biopsy device 100, the actuator 120 may be distally displaced with respect to the body member 110. When the actuator 120 is distally displaced, and the biopsy device 100 is in a primed configuration, trigger surfaces 129 of the actuator 120 interact with angled arm surfaces 149 of the pincer hub 140 such that the pincer hub arms 147 are displaced radially outward, until the pincer hub proximal catches 148 are no longer engaged with the priming catches 168 of the housing member 160. This allows the spring 190 to unload, transferring potential energy in the spring 190 to the pincer hub 140 as the pincer hub 140 is accelerated and moves in a distal direction.

As the pincer hub 140 is displaced distally, the pincer hub distal shoulder 144 impacts the needle hub distal catches 154, accelerating the needle hub 150. As further detailed below, acceleration of the needle hub 150 by an impact force may facilitate retrieval of quality tissue samples.

The interaction of the pincer hub distal shoulder 144 and needle hub catches 154 thus couple the pincer hub 140 and needle hub 150. After impact, the pincer hub 140 and needle hub 150 travel distally together until interaction between the needle hub 150 and the adjustable stop assembly 130 stops the distal movement of the needle hub 150. Specifically, the release member 134 of the adjustable stop assembly 130 may comprise a stop surface 137 which interacts with the needle hub distal end 159. As further detailed below, these components may or may not directly interact. Specifically, a dampening element 170 may be disposed between the stop surface 137 and the needle hub distal end 159.

Figure 6:
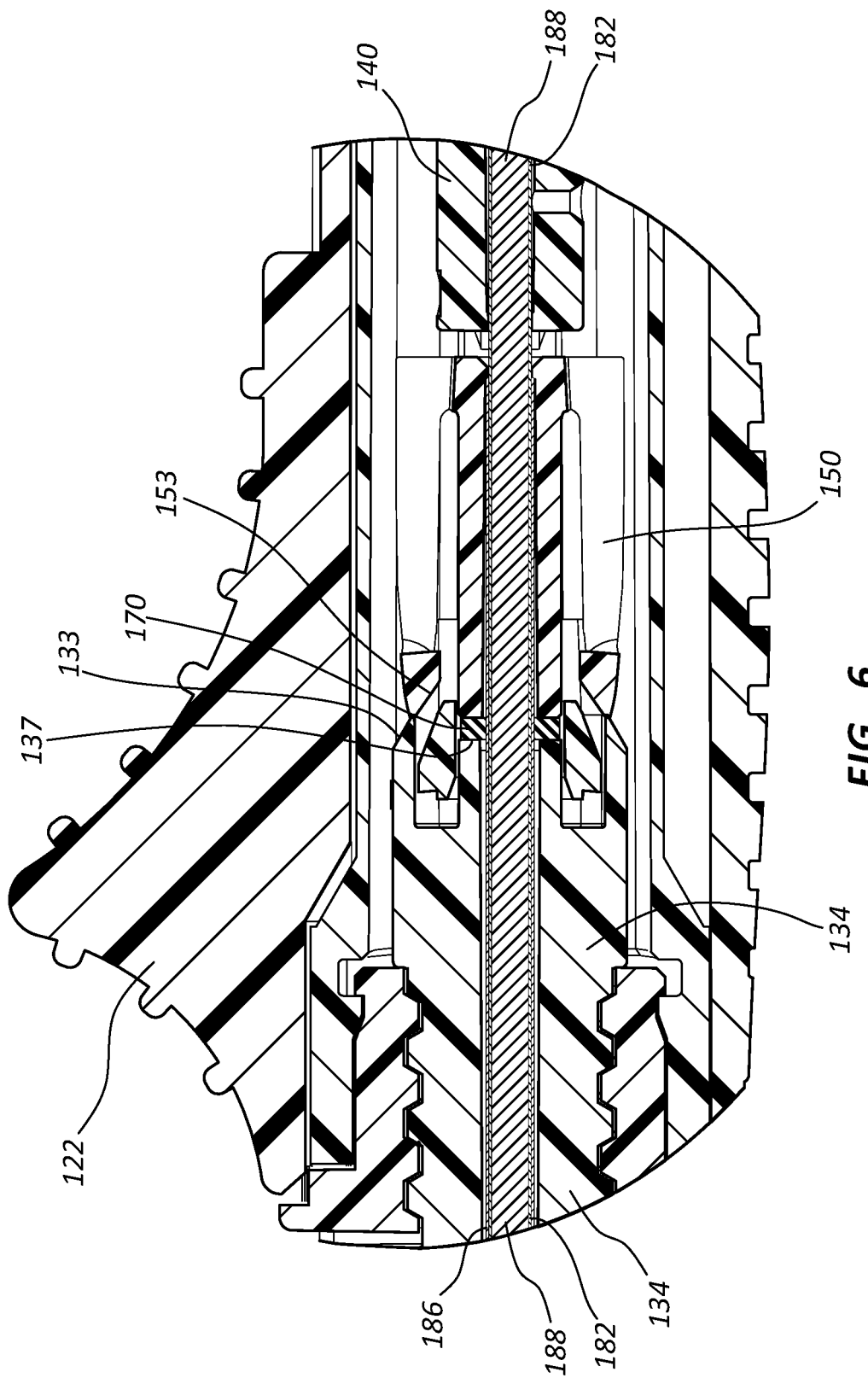
FIG. 6 is an enlarged section view of a portion of FIG. 2, taken around line 6-6.

FIG. 6 is an enlarged section view of a portion of FIG. 2, taken around line 6-6. FIG. 6 shows the relationship between the release member 134, pincer hub 140, needle hub 150, and dampening element 170 in more detail. Other features also shown and described in connection with FIG. 2 are also shown in FIG. 6.

With reference to interaction between the needle hub 150 and the release member 134, the release member 134 may also interact with the pincer hub 140 to decouple the pincer hub 140 and the needle hub 150. Specifically, and with continued reference to FIG. 6 as well as FIGS. 2-5B, the release member 134 may comprise one or more release surfaces 133 which interact with the needle hub angled surfaces 153, displacing the needle hub arms 155 radially outward and decoupling the needle hub 150 and the pincer hub 140 by moving the needle hub distal catches 154 out of engagement with the pincer hub distal shoulder 144.

Once decoupled from the needle hub 150, the pincer hub 140 may continue distally beyond the needle hub 150 after interaction with the release member 134 stops displacement of the needle hub 150. The pincer hub 140 may continue until the pincer hub stop surface 145 contacts one or more of the needle hub stop surfaces 156, thus arresting the distal motion of the pincer hub 140. Thus, the pincer hub 140 may be configured to travel beyond the needle hub 150.

Once the biopsy device 100 has been triggered, it may be returned to a primed configuration by proximally displacing the actuator 120 as described above. Again, the actuator may comprise a distal input 122 and a proximal input 124. Either of these inputs 122, 124 may be manipulated in order to prime or trigger the biopsy device 100. The shape, grip, or position of these inputs 122, 124 may also facilitate or enable one-handed use of the biopsy device 100. For example, while gripping the body member 110, a user may displace the distal input 122 with a finger or thumb of the gripping hand, both to prime and to trigger the biopsy device 100. Additionally, a user may manipulate the safety tab 126 to prevent inadvertent triggering of the device during use. For example, when the biopsy device 100 is in a primed position, the safety tab 126 may be positioned such that distal displacement (or triggering) of the actuator 120 is inhibited.

The dampening element 170 may thus be disposed to dampen shock, tactile feedback or recoil, and/or noise associated with use of the biopsy device 100. The dampening element may comprise any shock-absorbing material, for example, elastomeric materials, resilient materials, foam, rubber, and so forth. Use of one or more dampening elements 170 may additionally reduce shock and wear on various components of the biopsy device 100. For example, in the depicted embodiment, the dampening element is disposed between the release member 134 and the needle hub 150 such that the dampening element 170 absorbs energy associated with impact of the needle hub 150 on the release member 134 to arrest the travel of the needle hub 150 after triggering. Use of a dampening element 170 may reduce deformation or wear on the needle hub 150 and/or the release member 134 due to this interaction.

In the illustrated embodiment, portions of the needle assembly 180 extend along a longitudinal axis of the biopsy device 100. For example, a trocar 188 extends along the axis of the biopsy device 100 and may be coupled to the housing member 160. Other cutting elements, such as a biopsy needle associated with the needle hub 160 and a pincer associated with the pincer hub 140, may be disposed around the trocar 188. Similarly, elements such as the pincer hub 140 and/or needle hub 150 may comprise a central lumen and may be disposed such that one or more of the members of the needle assembly 180 pass through the lumens of these components. Similarly, the dampening member 170 may comprise a lumen and may be disposed around the trocar 188 and one or more additional members of the needle assembly 180. In some embodiments the dampening member 170 may not be fixed coupled to any element, but rather allowed to float along the needle assembly 180. In other embodiments, the dampening member 170 may be coupled to the needle hub 150 or the release member 134. Still further, other dampening elements disposed at other positions within the biopsy device 100 are within the scope of this disclosure.

In some embodiments, manipulation of the adjustable stop assembly 130 may be configured to control the length of tissue sample severed by the biopsy device 100. For example, overall length of travel of the pincer hub 140 and needle hub 150 may be controlled or adjusted by the position of the release member 134 with respect to the housing member 160. As the length of travel of the pincer hub 140 and needle hub 150 is varied, the travel length of any cutting members coupled thereto is also varied.

The adjustable stop assembly 130 may be configured to make the position of the release member 134 adjustable along a continuous range. This range may be defined, for example, by threads on the release member 134. Interaction of threads on the release member 134 and mating threads coupled to the housing member 160 may vary the longitudinal position of the release member 134 with respect to the housing member 160 as the release member 134 is rotated with respect to the housing member 160. Thus, the adjustable stop assembly 130 may be configured such that a practitioner can adjust the length of the sample to be severed by the biopsy device 100, along a range related to the range of longitudinal displacement of the release member 134.

The adjustable stop assembly 130 may facilitate use of the biopsy device 100 in particular therapies or procedures. Again, in some embodiments, the adjustable stop assembly 130 may be adjustable over a continuous range, allowing a practitioner to configure the biopsy device 100 to sever a sample of any length within the range. For example, a practitioner may desire to sever a relatively short tissue sample, such as instances where obtaining a deeper sample would cause unwanted trauma to adjacent tissue. Thus, the practitioner may manipulate the position of the adjustable stop assembly 130 in order to obtain a sample of a desired length while avoiding severing tissue adjacent the sample. Embodiments that utilize distinct catches to position the release member 134 at particular intervals are also within the scope of this disclosure.

The adjustable stop assembly 130 may be adjustable over a continuous range of any length. For example, the adjustable stop assembly 130 may be configured to allow a practitioner to adjust sample length over a continuous range from 2 mm to 35 mm, including from 5 mm to 30 mm, and from 10 mm to 20 mm. Further, the sample length may be adjustable to lengths less than 2 mm or greater than 35 mm.

In the depicted embodiment the adjustable stop assembly 130 comprises a an adjustment shell 132 and a release member 134. The adjustment shell 132 may be coupled to the release member 134 such that rotation of the adjustment shell 132 causes rotation of the release member 134. Further, the components may be disposed such that while the release member 134 is allowed to displace longitudinally with respect to housing member 160, the longitudinal position of the adjustment shell 132 does not vary with respect to the housing member 160. For example, a ridge on the release member 134 may be displaced within a slot of the adjustment shell 132, such that the ridge and slot may transfer rotational displacement of the adjustment shell 132 without restraining longitudinal displacement of the release member 134.

Such an arrangement allows the release member 134 to be longitudinally displaceable with respect to the housing member 160 as the adjustment shell 132 and release member 134 are rotated (via interaction of mating threads of the release member 134 and housing member 160, for example) without longitudinal displacement of the adjustment shell 132. In the illustrated embodiment, indicia on the adjustment shell 132 correlate with the longitudinal displacement of the release member 134, allowing a practitioner to adjust and/or set the stroke length through rotation of the adjustment shell 132 and observation of the relative position of the indicia with respect to a reference on the release member 134. Adjustable stop assemblies 130 comprising tactile or audible feedback associated with rotation of the adjustable shell 132 are also within the scope of this disclosure.

As noted above, in the illustrated embodiment, the biopsy device 100 utilizes the spring 190 to store potential energy during use. Again, in some embodiments other energy sources, such as compressed gas, may be used in connection with, or in place of, a spring 190.

As also noted above, the biopsy device 100 may transfer force to the needle hub 150 through impact between the pincer hub 140 and the needle hub 150. Again, the pincer hub 140 may be accelerated by transfer of potential energy from another source (such as the spring 190) directly to the pincer hub 140. A portion of the kinetic energy associated with the moving pincer hub 140 may be transferred to the needle hub 150 at impact. Accordingly, the biopsy device 100 may be configured to quickly transfer force to a cutting member, and thus may be configured to limit deformation of the tissue sample during cutting. In some instances, a needle or other cutting member will more cleanly sever tissue when it is moving at a threshold speed, or cutting speed. During acceleration of the needle, the needle may thus move through tissue by compressing or otherwise deforming the tissue, rather than severing the tissue. An impact force may very quickly accelerate the needle, minimizing any such deformation. For example, by accelerating the needle hub 150 with an impact force, initial deformation of tissue adjacent a needle coupled to the needle hub 150 may be minimized.

The biopsy device 100 may thus first accelerate the pincer hub 140, allowing the pincer hub 140 to reach a particular speed before impacting the needle hub 150. The spring 190 may be configured to accelerate the pincer hub 140 to an impact speed over a distance (such as the distance the pincer hub 140 is displaced prior to impact) that may allow use of a spring having a relatively small spring constant, as the pincer hub 140 is not required to reach impact speed prior to impact with the needle hub 150. The "impact speed" of the pincer hub 140 may be defined as the speed at which the pincer hub 140 travels in order to impart an impact force sufficient to accelerate the needle hub 150 to cutting speed. Thus the initial distance associated with accelerating the pincer hub 140, through transfer of energy from the spring 190, will not necessarily result in the deformation of tissue during initial acceleration of the biopsy device 100 components.

Additionally, a biopsy device 100 utilizing acceleration by impact may facilitate severing tissue samples of a variety of lengths. The impact configuration may accelerate cutting members associated with the device to cutting speed without substantially displacing the needle. Thus, the biopsy device 100 may be configured to sever particularly short samples, as the needle hub 150 reaches cutting speed without substantial displacement. By comparison, direct acceleration of a needle hub by a spring may require some displacement of the needle hub before the needle reaches cutting speed. Thus, the minimum sample length may be at least as long as the displacement needed to bring such a needle to cutting speed. Further, the biopsy device 100 may be configured such that the needle maintains a substantially uniform cutting speed during the severing of an entire sample, rather than accelerating during the first portion of the severing. Samples severed by uniform cutting speeds may be generally more uniform than samples severed by accelerating cutting members, which may deform a portion of the sample.

The potential energy stored in the spring 190 may be expressed by the equation $E=(0.5)kx^2$, where k is the spring constant and x the displacement of the spring 190 in the compressed state. The energy associated with the pincer hub 140 (and pincer components coupled thereto) after it is accelerated by the spring 190 may be expressed as $E=(0.5)mV^2$ where m is the mass of the components coupled to the pincer hub 140 and V is the velocity of the pincer hub 140. The exponential factor associated with the potential energy of the spring 190 may also facilitate use of springs with relatively small spring constants in the biopsy device 100. Use of springs with relatively small spring constants may make the biopsy device 100 easier to prime, and may reduce shock and recoil during use.

Figure 7:
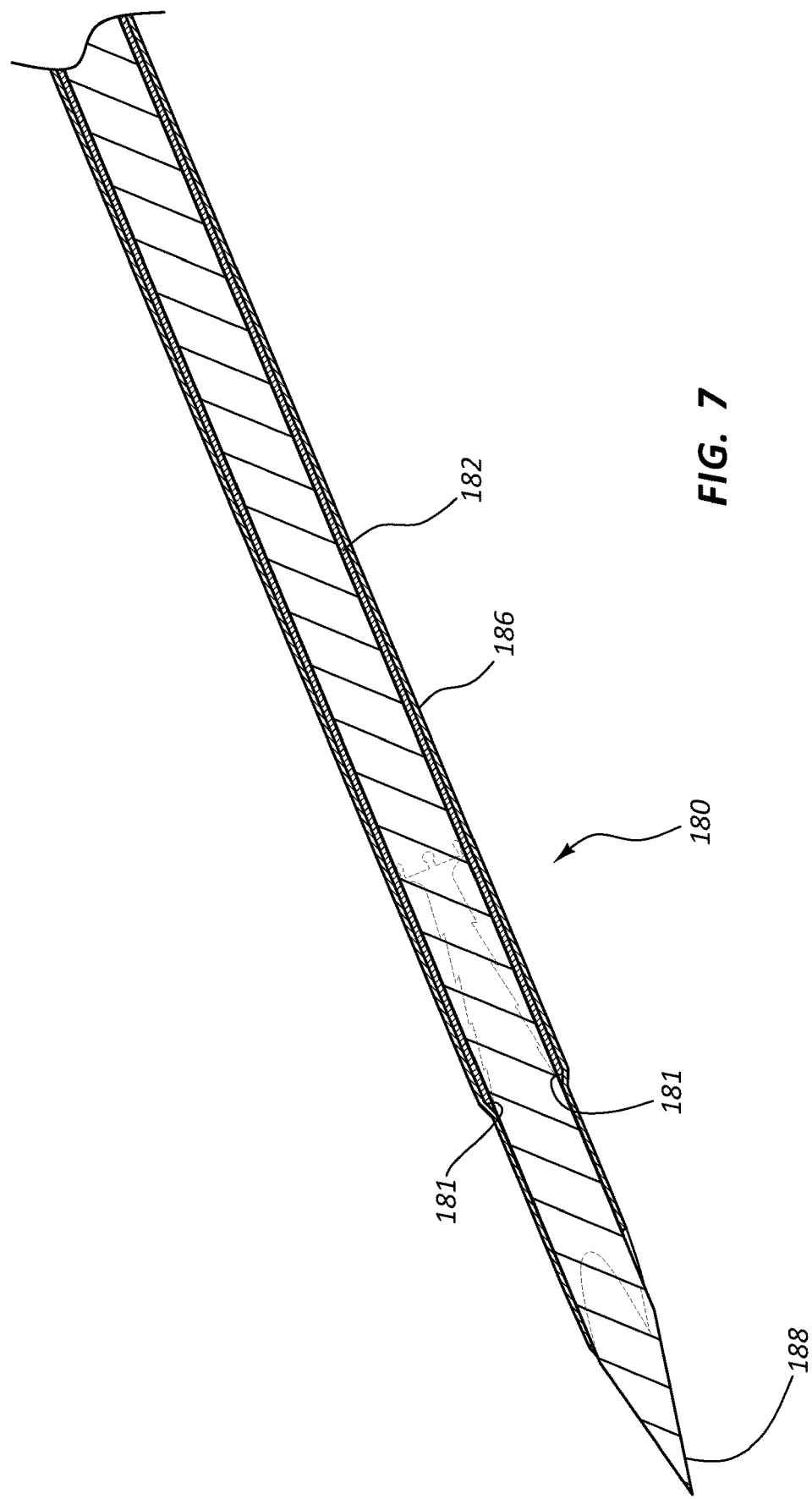
FIG. 7 is a portion of the needle assembly of the biopsy device of FIG. 1, in a primed configuration.

As detailed above, the actuation assembly may be configured such that the pincer hub 140 travels distally a set distance after the needle hub 150 impacts the release member 134, including embodiments wherein the dampening element 170 is disposed between the needle hub 150 and the release member 134. In some embodiments, the needle assembly 180 may thus be designed such that a needle associated with the needle hub 150 severs the longitudinal portion of a sample, while a pincer associated with the pincer hub 140 severs the distal end of the sample after the longitudinal portion is initially cut. FIGS. 7, 8A and 8B detailed below illustrate an exemplary configuration of a needle 186, a pincer 182, and a trocar 188. Various arrangements of cutting members and needle assemblies having members with differing lengths of travel are within the scope of this disclosure. The needle 186 may comprise a hollow cannula with a distal cutting edge configured to sever the longitudinal portion of a tissue sample, and the pincer 182 may comprise a hollow cannula with a distal cutting portion configured to sever the distal portion of a tissue sample, as further detailed below.

FIG. 7 is a cross-sectional view of a portion of the needle assembly 180 of the biopsy device 100 of FIG. 1. In the configuration of FIG. 7, the needle assembly 180 is disposed in a primed configuration, as opposed to the fired configuration shown in FIGS. 1-3. The needle assembly 180 comprises a trocar 188, a needle 186, and a pincer 182. The trocar 188 may extend along the longitudinal axis of the needle assembly 180 and along the longitudinal axis of the biopsy device (100 of FIG. 2). The trocar 188 may be fixed to the housing member (160 of FIG. 2), such that the needle 186 and pincer 182 are displaced relative to the trocar 188 when the needle hub (150 of FIG. 2) and the pincer hub (140 of FIG. 2) are displaced with respect to the housing member (160 of FIG. 2).

Again, in the configuration shown in FIG. 7, the biopsy device (100 of FIG. 2) is in a primed configuration as discussed above, meaning the pincer hub (140 of FIG. 2) and the needle hub (150 of FIG. 2) are drawn back in a proximal direction. (It is noted that this is a different configuration than depicted in FIG. 2 as discussed above.) In the primed configuration the trocar 188 extends from the distal end of the needle assembly 180. With the trocar 188 so disposed, the needle assembly 180 may be advanced through tissue (for example, percutaneously or otherwise through tissue) and disposed adjacent tissue to be sampled.

When the biopsy device (100 of FIG. 2) is triggered as discussed above, the needle 186 is advanced into the tissue, severing the longitudinal portion of the tissue sample. As the trocar 188 is coupled to the housing member (160 of FIG. 2) the needle 186 extends beyond the trocar 188 as the needle hub (150 of FIG. 2) is displaced with respect to the housing member (160 of FIG. 2). As detailed above, the needle 186 is accelerated by impact between the pincer hub (140 of FIG. 2) and the needle hub (150 of FIG. 2).

Initially, after triggering, the pincer 182 advances with respect to both the needle 186 and the trocar 188, prior to impact between the pincer hub (140 of FIG. 2) and the needle hub (150 of FIG. 2). The components may be positioned such that during the initial advancement of the pincer 182, the pincer remains proximal of a annular shoulder 181 of the needle 186. The annular shoulder 181 of the needle 186 comprises a portion of the needle 186 with a reduced inside diameter, as shown in the drawings and further detailed below. After impact, both the needle 186 and the pincer 182 advance into the tissue sample.

As detailed above, the needle 186 stops prior to the pincer 182, as the needle hub (150 of FIG. 2) contacts the release member (134 of FIG. 2) decoupling the needle hub (150 of FIG. 2) and the pincer hub (140 of FIG. 2) and arresting the forward motion of the needle hub (150 of FIG. 2). Again, the dampening element (170 of FIG. 2) may reduce shock as the needle 186 stops.

The pincer hub (140 of FIG. 2) travels a distance after the needle hub (150 of FIG. 2) stops, correlating to distal displacement of the pincer 182 with respect to the needle 186 at the end of the stroke. As detailed below, this displacement correlates to severing of a distal end of the sample by the pincer 182.

FIG. 8A shows the needle 186 and the pincer 182 in the primed configuration, though the trocar (188 of FIG. 7) is not shown in this view. In the primed configuration, the pincer 182 is proximal of the annular shoulder 181 of the needle 186. This proximal offset may correlate to the distance the pincer hub (140 of FIG. 2) travels before impact with the needle hub (150 of FIG. 2) such that the pincer 182 remains proximal of the annular shoulder 181 of the needle 186 until the needle 186 completes its stroke, severing the longitudinal position.

FIG. 8B shows the needle 186 and the pincer 182 at the end of a stroke, after the needle hub (150 of FIG. 2) and the pincer hub (140 of FIG. 2) have been decoupled and the pincer hub (140 of FIG. 2) has traveled distally after the needle hub (150 of FIG. 2) contacted the release member (134 of FIG. 2), including through interaction with the dampening element (170 of FIG. 2). This travel of the pincer hub (140 of FIG. 2) correlates with displacement of the pincer 182 with respect to the needle 186 such that the annular shoulder 181 displaces portions of the pincer 182 radially inward to sever the distal end of a sample.

Accordingly, the position of the needle assembly 180 elements in FIG. 7 and FIG. 8A correspond to a primed configuration while the relative positions shown in FIG. 8B correspond to a fired configuration. In an initial shipping configuration, pincer 182 may be disposed such that the pincer 182 is proximal of the annular shoulder 181, though the spring (190 of FIGS. 2-3) may not be in a loaded configuration, as further detailed above.

In the illustrated embodiment, the annular shoulder 181 corresponds to a region of the needle 186 with a reduced diameter. This reduced diameter extends from the annular shoulder 181 to the distal end of the needle 186 in the illustrated embodiment. In other embodiments, protrusions, an annular ring, or other features may be disposed to displace the portions of the pincer 182.

Repriming the biopsy device (100 of FIG. 2) would return the needle assembly to the configuration shown in FIG. 7, retracting the pincer 182 and needle 186 such that the trocar 188 would push the sample out of the needle 186.

FIG. 9A is a perspective view of another embodiment of a pincer, and FIG. 9B is a detailed view of a distal end portion of the pincer of FIG. 9A taken through line 9B-9B that can, in certain respects, resemble components of the pincer 182 described in connection with FIGS. 1-8B. It will be appreciated that all the illustrated embodiments may have analogous features. Accordingly, like features are designated with like reference numerals, with the leading digit of the reference numerals incremented by 1. For instance, the pincer is designated as "182" in FIGS. 1-8B, and an analogous pincer is designated as "282" in FIGS. 9A and 9B. Relevant disclosure set forth above regarding similarly identified features thus may not be repeated hereafter. Moreover, specific features of the pincer 182 and related components shown in FIGS. 9A and 9B may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the pincer 282 of FIGS. 9A and 9B. Any suitable combination of the features, and variations of the same, described with respect to the pincer 282 and components illustrated in FIGS. 9A and 9B can be employed with the pincer 182 and components of FIGS. 1-8B, and vice versa. This pattern of disclosure applies equally to further embodiments depicted in subsequent figures and described hereafter.

Specifically, it is within the scope of this disclosure to utilize pincer 282 in place of pincer 182 in the biopsy device 100 and needle assembly 180 discussed in connection with FIGS. 1-8B.

As depicted, the pincer 282 may comprise a plurality of sectioning elements 284. Additionally, the pincer 282 may comprise one or more spiral cuts 285 disposed along at least a portion or portions of the length of the pincer 282. In the illustrated embodiment, the spiral cut 285 is disposed along at least a portion of the length of the pincer 282 at a position proximal to the sectioning elements 284. In various embodiments, the pincer 282 may comprise a spiral cut 285 disposed proximal of the one or more sectioning elements 284. In some embodiments, the spiral cut 285 may be disposed at a distance sufficiently proximal in relation to the sectioning elements 284 such that the spiral cut 285 does not, or does not substantially, interfere with or damage a tissue sample.

In some embodiments, the pincer 282 may comprise one or more sectioning elements 284 (e.g., one, two, three, four, five, six, or more sectioning elements 284). In the illustrated embodiment, the pincer 282 comprises six sectioning elements 284. As discussed above, the sectioning elements 284 may be coupled to the pincer 282. In some configurations, the sectioning elements 284 and the pincer 282 may be integrally formed from a single piece of material. In certain embodiments, at least one of the sectioning elements 284 may comprise a sharp distal portion. As depicted in FIGS. 9A and 9B, the sectioning elements 284 can comprise a pointed or tapered distal portion. At least one of the sectioning elements 284 may also comprise at least one sharp lateral edge portion. In some embodiments, the at least one sharp lateral edge portion may be angled.

With continued reference to FIGS. 9A and 9B, the sectioning elements 284 can comprise a plurality of angled lateral edge portions. For example, the lateral edge portions of the section elements 284 may be serrated or notched. Such a configuration of the one or more sectioning elements 284 may facilitate the cutting or severing of body tissue by the sectioning elements 284.

As discussed above with respect to the sectioning elements 284, the shape of the sectioning elements 284 may also be configured such that the sectioning elements 284 may be simultaneously, or substantially simultaneously, inwardly displaced toward each other to sever the second portion of the tissue sample. Interaction with other components of a biopsy device or needle assembly (such as the annular shoulder 181 of FIG. 7) may also be configured to inwardly displace the sectioning elements 284. In some embodiments, an annular shoulder (181 of FIG. 7) on the inside of a needle (186 of FIG. 7) may be replaced with an annular ring around the inside diameter of the needle (186 of FIG. 7) discrete protrusions, or other features.

In some embodiments, the spiral cut 285 may extend completely through a wall of the pincer 282. In some other embodiments, the spiral cut 285 may only extend partially through the wall of the pincer 282. For example, the spiral cut 285 may form a groove along a portion of the length of the pincer 282. In yet other embodiments, one or more portions of the spiral cut 285 may extend completely through the wall of the pincer 282 while one or more other portions of the spiral cut 285 may form a groove in the wall of the pincer 282.

In certain embodiments, disposition of the spiral cut 285 along the pincer 282 can form a spring, or a spring-like portion, along the pincer 282. The spiral cut 285 may add or provide compliance or elasticity to the pincer 282 and/or the biopsy needle assembly. For example, the spiral cut 285 may improve or increase tolerances of one or more of the components of the pincer 282 and/or the biopsy needle assembly. Such improved tolerances may facilitate advancement or displacement of the pincer 282 and/or the biopsy needle assembly through a body tissue. In various embodiments, the spiral cut 285 may absorb impact or shock to one or more of the pincer 282, other components of the biopsy needle assembly, and/or the biopsy needle assembly. For example, upon advancement or displacement of at least a portion of the biopsy needle assembly through a body tissue of a patient, at least a portion of the spiral cut 285 may compress or be configured to compress (i.e., the spiral cut 285 may compress longitudinally, thus shortening the length of the pincer 282). In certain embodiments, the spiral cut 285 can be configured to longitudinally compress in response to relative displacement of the outer tubular member, or another component of the biopsy needle assembly, in relation to the pincer 282.

Furthermore, in connection with the dampening element (170 of FIGS. 2-3) a pincer 282 comprising a spiral cut 285 may add additional compliance and shock absorption to a biopsy device. Such shock absorption may increase sample quality, lessen wear on components, and reduce recoil and shock.

One or more forces may result in or cause compression of the spiral cut 285. For example, inertia of the pincer 282 as it is advanced into a body tissue can result in compression of the spiral cut 285. Displacement of the pincer 282 in relation to the needle (such as 186 of FIG. 2) and/or the trocar (such as 188 of FIG. 2) may also result in compression of the spiral cut 285. For example, friction between an outside surface of the pincer 282 and an inside surface of the outer tubular member may result in compression of the spiral cut 285. Furthermore, force used to advance or displace the sectioning elements 284 of the pincer 282 over or past the an annular shoulder (181 of FIG. 2) or other features on the inside diameter of a needle (such as 186 of FIG. 2) can also result in compression of the spiral cut 285.

Additionally, at least a portion of the spiral cut 285 may rotate, or be configured to rotate, upon compression of the spiral cut 285. Rotation of the spiral cut 285 may also cause or result in rotation of the sectioning elements 284 around a central axis of the pincer 282. This rotation may facilitate uniform, or substantially uniform, severing of the distal end of a tissue sample as the spiral cut 285 rotates back to an initial position as the spiral cut uncompresses at the end of a stroke.

In some embodiments, the spiral cut 285 and/or the sectioning elements 284 may rotate, or be configured to rotate, between 0° and plus or minus 90°. In some embodiments, the spiral cut 285 and/or the sectioning elements 284 may rotate, or be configured to rotate, between 0° and plus or minus 45°; between 0° and plus or minus 30°; between 0° and plus or minus 15°; between 0° and plus or minus 5°; or another suitable degree of rotation. Again, rotation of the sectioning elements 284 through a body tissue may form or result in a cleaner or sharper cut in a tissue sample, as rotation of the sectioning elements 284 may sever along a complete, or a substantially complete, circumference of the distal end of the tissue sample.

Various methods and procedures are within the scope of this disclosure. Methods of priming the biopsy device 100 (as detailed above), advancing the biopsy device 100 through tissue, and triggering the biopsy device 100 (as also detailed above) are all within the scope of this disclosure. Further methods of obtaining a sample through impact acceleration of cutting members and methods of dampening shock or recoil through interaction of the elements described above are all within the scope of this disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art, and having the benefit of this disclosure, that changes may be made to the details of the above-described embodiments without departing from the underlying principles of the disclosure herein.

The invention claimed is:

1. A tissue biopsy device, comprising:
a handle configured to be grasped by a user;
a needle assembly operably coupled to the handle, the needle assembly configured to sever a tissue sample; and
an actuation assembly operably coupled to the handle and needle assembly, the actuation assembly comprising:
a biasing member;
a first hub member configured to be displaced by the biasing member when the actuation assembly is actuated;
a second hub member coupled to the needle assembly, the first hub member configured to displace at least a portion of the needle assembly when the first hub member impacts the second hub member,
wherein the second hub member is partially disposed within a lumen of the first hub member, and wherein the lumen of the first hub member is substantially concentric with a lumen of the second hub member, and
wherein the lumen of the first hub member is substantially concentric with a longitudinal axis of the first hub member; and
a dampening member configured to absorb a portion of a kinetic energy of the second hub member to arrest a motion of the second hub member with respect to the handle.

2. The biopsy device of claim 1, wherein the first hub member is displaced over a distance before impacting the second hub member.

3. The biopsy device of claim 1, wherein the biasing member does not directly exert a force on the second hub member when the device is actuated.

4. The biopsy device of claim 1, wherein a kinetic energy associated with the first hub member is transferred to the second hub member to accelerate the second hub member when the device is actuated.

5. The biopsy device of claim 1, wherein the needle assembly comprises a first hollow cannula coupled to the first hub member and a second hollow cannula coupled to the second hub member, wherein the first hollow cannula is configured to sever a distal end of the tissue sample and the second hollow cannula is configured to sever a longitudinal portion of the tissue sample.

6. The biopsy device of claim 5, wherein the first hollow cannula further comprises a spiral cut wherein the spiral cut is configured to longitudinally compress in response to relative displacement of the first hollow cannula with respect to the handle.

7. The biopsy device of claim 6, wherein the compression of the spiral cut is configured to rotate one or more sectioning elements around a central axis of the first hollow cannula.

8. The biopsy device of claim 5, further comprising an adjustable stop member operably coupled to the handle, the adjustable stop member is adjustable over a continuous range to vary a length of travel of the second hub member.

9. The biopsy device of claim 8, wherein the dampening member is disposed between the second hub member and the adjustable stop member such that the dampening member absorbs a portion of the kinetic energy of the second hub member when interaction with the adjustable stop member arrests the motion of the second hub member with respect to the handle.

10. A tissue biopsy device comprising: a handle configured to be graspable by a user;
    a biasing member operably coupled to the handle, the biasing member configured to store a potential energy when the biopsy device is in a primed configuration;
    a first hub member operably coupled to the handle and to the biasing member, the device configured such that the first hub member impacts a second hub member when the biopsy device is actuated such that the second hub member is displaced relative to the handle,
    wherein the second hub member is partially disposed within a lumen of the first hub member, and
    wherein the lumen of the first hub member is substantially concentric with a lumen of the second hub member; and
    a dampening member operably coupled to the biopsy device;
    wherein, during operation, the potential energy stored in the biasing member is at least partially transferred to a kinetic energy associated with the first hub member, the kinetic energy associated with the first hub member is at least partially transferred to the second hub member through impact between the first hub member and the second hub member, and a kinetic energy associated with the second hub member is at least partially absorbed by the dampening member.

11. The biopsy device of claim 10, wherein the first hub member is displaced over a distance before impacting the second hub member.

12. The biopsy device of claim 10, wherein a longitudinal travel distance of the second hub member is adjustable over a continuous range.

13. The biopsy device of claim 10, wherein the first hub member travels a longitudinal distance after motion of the second hub member is arrested.

14. A method of obtaining a tissue sample through actuation of a biopsy device, the method comprising:
    releasing a first hub member such that a biasing member displaces the first hub member a first longitudinal distance along the biopsy device;
    impacting the first hub member on a second hub member such that the second hub member is displaced a second longitudinal distance along the biopsy device, wherein a cylindrical portion of the second hub member is partially disposed within a lumen of the first hub member, and wherein the lumen of the first hub member is substantially concentric with a lumen of the second hub member: and
    absorbing a portion of an energy associated with the second hub member with a resilient dampening element.

15. The method of claim 14, further comprising storing potential energy in the biasing member prior to releasing the first hub member.

16. The method of claim 14, further comprising displacing a first hollow cannula coupled to the first hub member to sever a first portion of a tissue sample.

17. The method of claim 16, further comprising displacing a second hollow cannula, releasably coupled to the first hollow cannula, the second hollow cannula displaced such that the second hollow cannula severs a second portion of the tissue sample.

18. The method of claim 17, further comprising rotating a portion of the first hollow cannula during severing of the first portion of the tissue sample.

19. The method of claim 17, wherein the second hollow cannula is automatically decoupled from the first hollow cannula after the second hollow cannula travels a longitudinal distance.

20. The method of claim 14, further comprising adjusting the biopsy device to control a length of the tissue sample by adjusting a position of a stop member, over a continuous range, wherein the stop member interacts with the second hub member.

\* \* \* \* \*